(12) United States Patent
Chang et al.

(10) Patent No.: US 9,526,889 B2
(45) Date of Patent: Dec. 27, 2016

(54) ELECTROMAGNETIC STIMULATION DEVICE FOR CHANGING NERVE THRESHOLD

(71) Applicant: GiMer Medical Co. Ltd., Taipei (TW)

(72) Inventors: Chi-Heng Chang, Taipei (TW); Wei-Tso Lin, Taipei (TW); Chan-Yi Cheng, Taipei (TW); Chii-Wann Lin, Taipei (TW); Yeong-Ray Wen, New Taipei (TW)

(73) Assignee: GiMER MEDICAL CO., LTD., New Taipei (TW)

( * ) Notice: Subject to any disclaimer, the term of this patent is extended or adjusted under 35 U.S.C. 154(b) by 49 days.

(21) Appl. No.: 14/049,235

(22) Filed: Oct. 9, 2013

(65) Prior Publication Data

US 2015/0100112 A1    Apr. 9, 2015

(51) Int. Cl.
*A61N 1/05* (2006.01)
*A61N 1/36* (2006.01)
*A61N 1/06* (2006.01)

(52) U.S. Cl.
CPC .............. *A61N 1/0551* (2013.01); *A61N 1/06* (2013.01); *A61N 1/36071* (2013.01)

(58) Field of Classification Search
CPC .. A61N 1/0456; A61N 1/0551; A61N 1/3605; A61N 2/006
See application file for complete search history.

(56) References Cited

U.S. PATENT DOCUMENTS

| | | | |
|---|---|---|---|
| 5,776,170 A * | 7/1998 | MacDonald | A61N 1/36021 607/46 |
| 6,246,912 B1 * | 6/2001 | Sluijter | A61N 1/36017 607/100 |
| 2005/0154425 A1 * | 7/2005 | Boveja | A61N 1/36082 607/45 |
| 2006/0149337 A1 * | 7/2006 | John | 607/45 |
| 2009/0062886 A1 * | 3/2009 | O'Handley et al. | 607/51 |
| 2014/0039579 A1 * | 2/2014 | Mashiach et al. | 607/61 |

FOREIGN PATENT DOCUMENTS

| | | |
|---|---|---|
| CN | 1138829 A | 12/1996 |
| CN | 101610810 A | 12/2009 |
| WO | WO 95/19804 | 7/1995 |
| WO | WO 2008/094345 A1 | 8/2008 |

* cited by examiner

*Primary Examiner* — Christopher D Koharski
*Assistant Examiner* — Natasha Patel
(74) *Attorney, Agent, or Firm* — Muncy, Geissler, Olds & Lowe, P.C.

(57) ABSTRACT

The electromagnetic stimulation device contains at least a positive electrode and at least a negative electrode. An insulating gap having width of a first distance is maintained between the positive and negative electrodes. The positive and negative electrodes are at least at a second distance away from a nerve to be stimulated. A preset voltage is applied to the positive and negative electrodes so that a low-power, low-temperature, high-frequency electromagnetic field covering and stimulating the nerve is produced between the positive and negative electrodes. By the stimulation of the low-power, low-temperature, high-frequency electromagnetic field, the nerve's threshold is increased, the nerve's transmission capability is reduced, and therefore the nerve pain is effectively eased.

16 Claims, 13 Drawing Sheets

```
┌─────────────────────────────────────┐
│   Providing at least an electromagnetic │
│  stimulation device having at least a positive │
│ electrode and at least a negative electrode, the │ ~100
│      positive and negative electrodes being     │
│         separated by a first distance.          │
└─────────────────────────────────────┘
                    ⇩
┌─────────────────────────────────────┐
│  Positioning the electromagnetic stimulation  │
│    device so that the positive and negative    │
│   electrodes are at least at a second distance │ ~110
│         away from a nerve to be stimulated.    │
└─────────────────────────────────────┘
                    ⇩
┌─────────────────────────────────────┐
│     Applying a preset voltage of no more than  │
│  10V and of a frequency between 200 KHz and    │
│   800 KHz to the electromagnetic stimulation   │
│        device so that an electromagnetic field │ ~120
│           covering and stimulating the nerve is │
│       produced between the positive and negative │
│                    electrodes.                  │
└─────────────────────────────────────┘
```

FIG.1

ELECTROMAGNETIC STIMULATION DEVICE FOR CHANGING NERVE THRESHOLD (a) Technical Field of the Invention The present invention is generally related to nerve stimulation by electromagnetic field, and more particular to a device of applying electromagnetic stimulation to increase nerve threshold.

(b) Description of the Prior Art

The human nerve system provides transmission paths for the commands issued from the brain. The human nerve has a threshold and the threshold is often reduced around a damaged spot of the nerve. Therefore, uncomfortable pain or ache is frequently and easily felt at this spot. After a period of time, this spot would become a source of chronic pain.

Clinically, an approach called Continuous Radiofrequency (CRF) or Radiofrequency Ablation is widely applied to ease various nerve pains. The approach inserts a pin into the proximity of related nerve tissue, applies continuous, high-frequency signal to create high temperature so as to destroy the nerve tissue, thereby alleviating the nerve pain. However, due to the human body's self-repair function, the destroyed nerve tissue will try to heal itself. When this happens, newly developed tissue grows randomly on the destroyed tissue, and it is quite common that a neuroma is formed. The neuroma, once formed, often oppresses the nerve system and causes even more serious pain.

Another conventional clinical approach is the so-called Pulsed Radiofrequency (PRF) where one electrode is inserted into the proximity of a nerve tissue. Then, a radiofrequency signal of 45V is employed so that the nerve tissue is stimulated twice every second, and for 20 ms every stimulation. By using intermittent pulses, the temperature of the stimulation process does not exceed 42° C., avoiding the high temperature's damaging or destroying the nerve tissue, and as such preventing the occurrence of post-operation neuroma.

One example is U.S. Pat. No. 6,246,912, titled "Modulated high frequency tissue modification," which teaches the connection of a high-frequency pulse generator 11 to a positive electrode pole 1 and a negative ground pad 16, the insertion of the electrode pole 1 into human body so that a terminal 2 of the electrode pole 1 is at a nerve spot to be treated, and the attachment of the ground pad 16 externally to the human body so as to form an electrical loop. Then, the nerve spot is simulated by a train of electrical pulses of a few dozens of volts through the terminal 2. In the process, the temperature is controlled so that the nerve tissue is not damaged or destroyed by high temperature. However, this can be achieved only when the duration of the pulses and the intermittent delay between pulses are precisely controlled.

SUMMARY OF THE INVENTION

Therefore a novel electromagnetic stimulation device is provided to obviate the shortcomings of the prior arts. The electromagnetic stimulation device contains at least a positive electrode and at least a negative electrode. An insulating gap is positioned between the positive and negative electrodes so that they are separated by a first distance. The positive and negative electrodes are at least at a second distance away from a nerve to be stimulated. A preset voltage is applied to the positive and negative electrodes so that a low-power, low-temperature, high-frequency electromagnetic field covering and stimulating the nerve is produced between the positive and negative electrodes. The preset voltage is no more than 10V and has a frequency between 200 KHz and 800 KHz. By the stimulation of the low-power, low-temperature, high-frequency electromagnetic field, the nerve's threshold is increased, the nerve's transmission capability is reduced, and therefore the nerve pain is effectively eased.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become apparent to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

FIG. 1 is a flow diagram showing an operation scenario of an electromagnetic stimulation device according to the present invention.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 2:
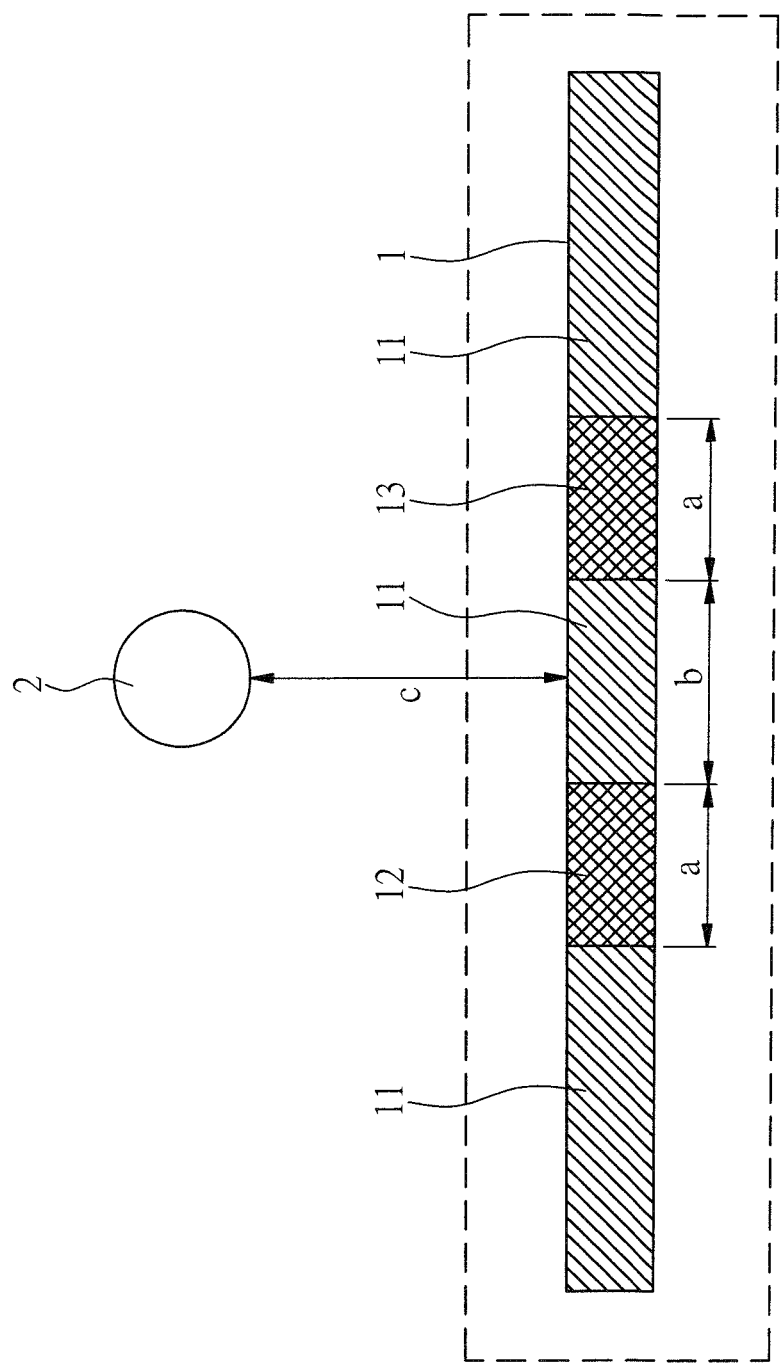
FIG. 2 is a schematic diagram showing an electromagnetic stimulation device according to the present invention.

As shown in FIGS. 1 and 2, an electromagnetic stimulation device for changing nerve threshold is described as follows.

The electromagnetic stimulation device 1 contains at least a positive electrode 12 and at least a negative electrode 13 configured on an insulating member 11. The positive and negative electrodes 12 and 13 are separated by an insulating gap having width of a first distance (b). The positive and negative electrodes 12 and 13 are therefore separated by the first distance (b). The first distance (b) is between 3 mm and 7 mm. The positive and negative electrodes 12 and 13 are at least at a second distance (c) away from a nerve 2 to be stimulated. The second distance (c) is no more than 10 mm. A preset voltage is applied to the positive and negative electrodes 12 and 13. The preset voltage is no more than 10V and has a frequency between 200 KHz and 800 KHz. Then, a low-power, low-temperature, high-frequency electromagnetic field covering and stimulating the nerve 2 is produced between the positive and negative electrodes 12 and 13.

Preferably, the preset voltage is between +3V and +10V, or between −3V and −10V, and has a frequency between 200 KHz and 800 KHz.

An embodiment of the present invention is described as follows. The electromagnetic stimulation device 1 is electrically connected to an external power supply which provides the preset voltage of no more than 10V with a frequency between 200 KHz and 800 KHz. A low-power, low-temperature, high-frequency electromagnetic field is produced between the positive and negative electrodes 12 and 13 of the electromagnetic stimulation device 1. Each of the positive and negative electrodes 12 and 13 has a width (a) between 1 mm and 3 mm.

An operation scenario of the electromagnetic stimulation device 1 is described as follows.

In step 100, at least an electromagnetic stimulation device 1 is provided. The electromagnetic stimulation device 1 contains at least a positive electrode 12 and at least a negative electrode 13. The positive and negative electrodes 12 and 13 are separated by an insulating gap having width of a first distance (b). The positive and negative electrodes 12 and 13 are therefore separated by the first distance (b).

In step 110, the electromagnetic stimulation device 1 is positioned so that the positive and negative electrodes 12 and 13 are at least at a second distance (c) away from a nerve 2 to be stimulated.

In step 120, a preset voltage is applied to the positive and negative electrodes 12 and 13. The preset voltage is no more than 10V and has a frequency between 200 KHz and 800 KHz. Then, a low-power, low-temperature, high-frequency electromagnetic field covering and stimulating the nerve 2 is produced between the positive and negative electrodes 12 and 13.

The low-power, low-temperature, high-frequency electromagnetic field covers the nerve 2 so that the nerve 2 is stimulated by the electromagnetic field without damaging the nerve 2's tissue cells. As such, the production of biomolecules from the nerve 2 is inhibited, the nerve threshold around nerve 2 is modified and increased, and the transmission capability around nerve 2 is reduced, effectively lessening the nerve pain of a user.

Figure 3:
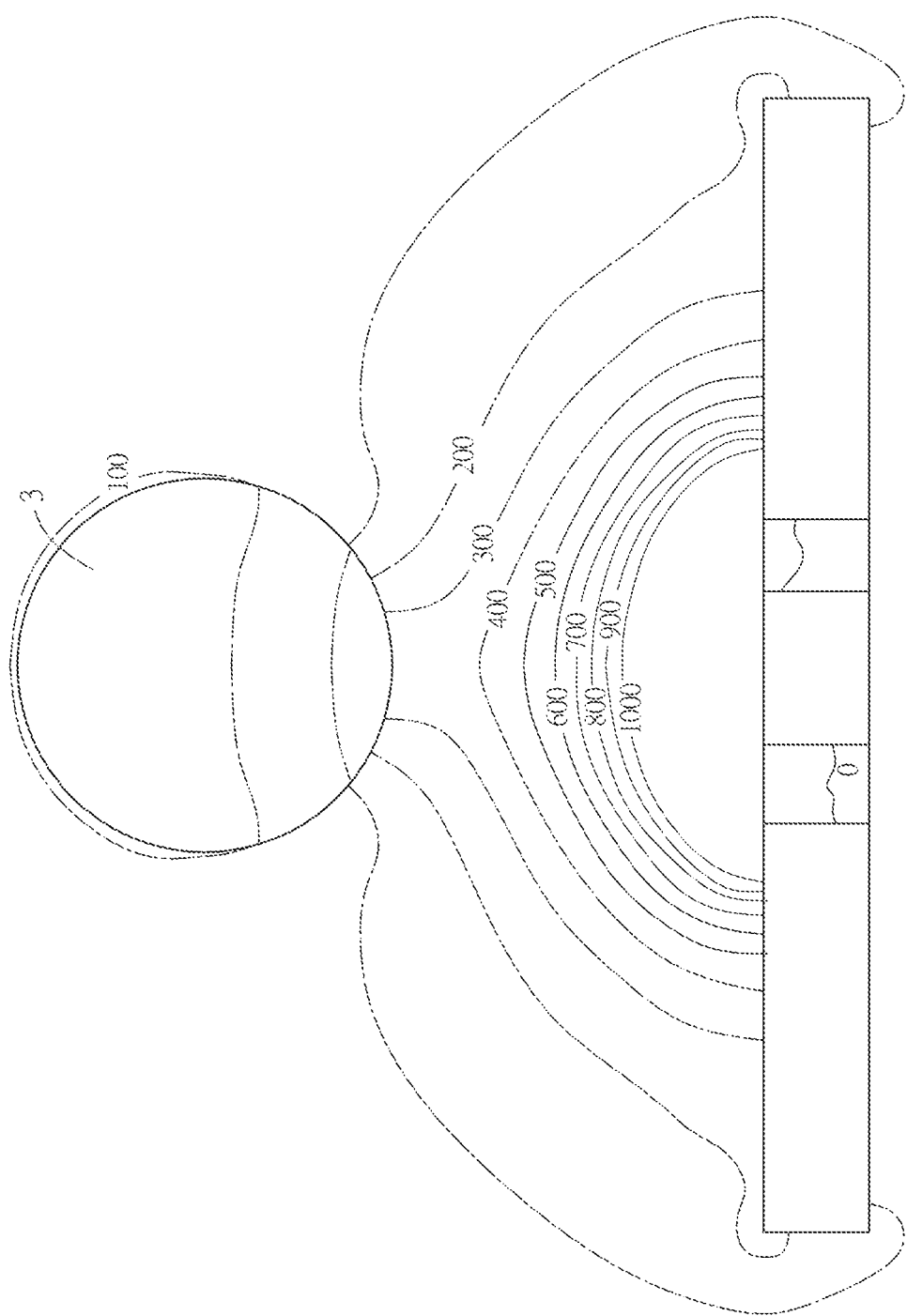
FIG. 3 is a graph showing the strength and pattern of the electromagnetic field produced by the electromagnet stimulation device of FIG. 2 where the distance between the device's electrodes is of a shorter distance.
Figure 4:
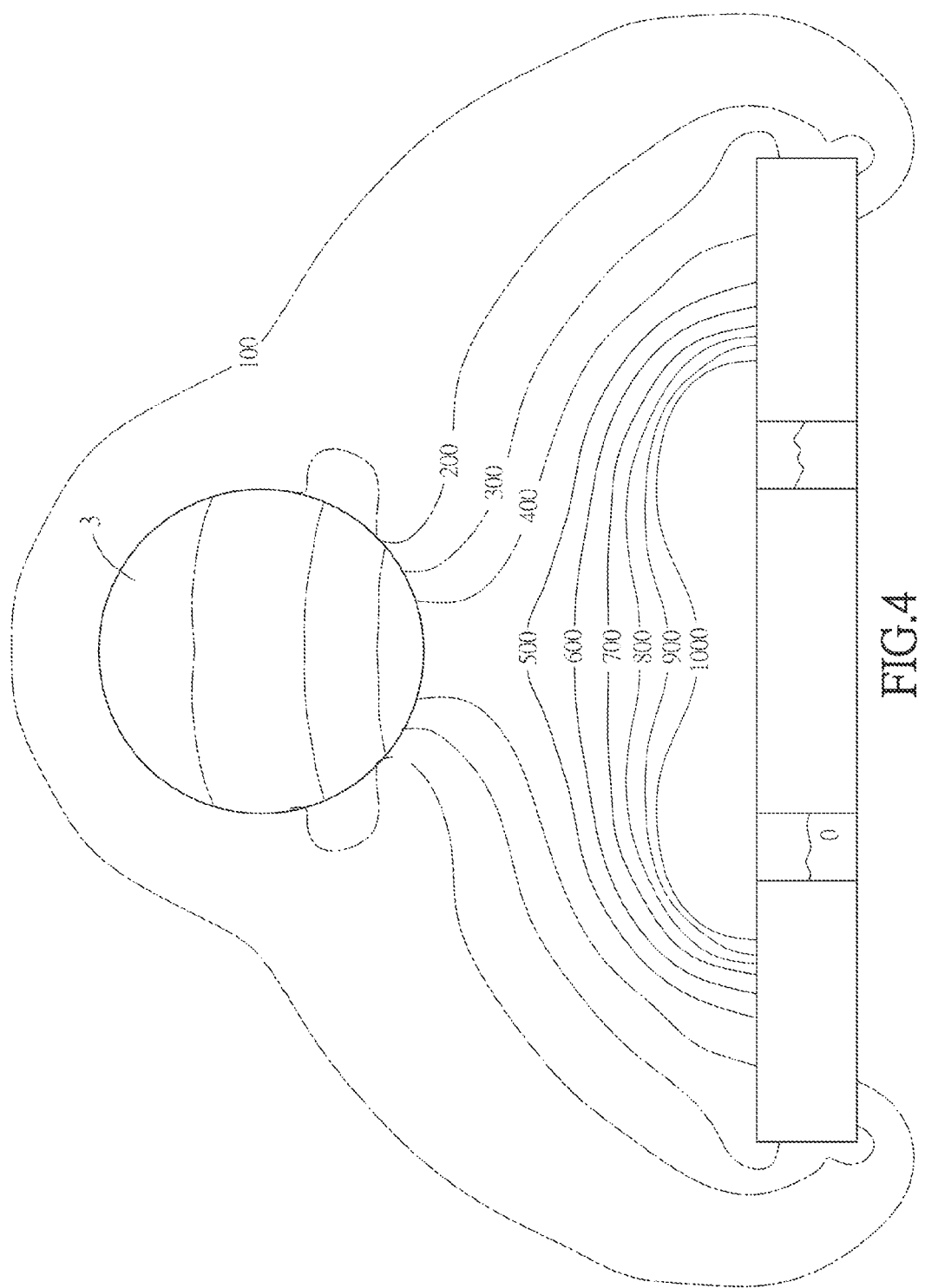
FIG. 4 is a graph showing the strength and pattern of the electromagnetic field produced by the electromagnetic stimulation device of FIG. 2 where the distance between the device's electrodes is of a greater distance.

The electromagnetic field's field pattern can be adjusted by selecting appropriate electrode width (a), the first distance (b), and the second distance (c). Another embodiment of the present invention is described as follows. The preset voltage is set to 5V with frequency 500 KHz. The electrode width (a) of the positive and negative electrodes 12 and 13, and the second distance (c) are fixed. Then, as shown in FIG. 3, when the first distance (b) between the positive and negative electrodes 12 and 13 is smaller, the electromagnetic field covers a portion of the to-be-stimulated nerve 2. On the other hand, when the first distance (b) is larger, as shown in FIG. 4, the electromagnetic field entirely covers the nerve 2. Additionally, the strength of the electromagnetic field is stronger as it is closer to the positive and negative electrodes 12 and 13.

Figure 5:
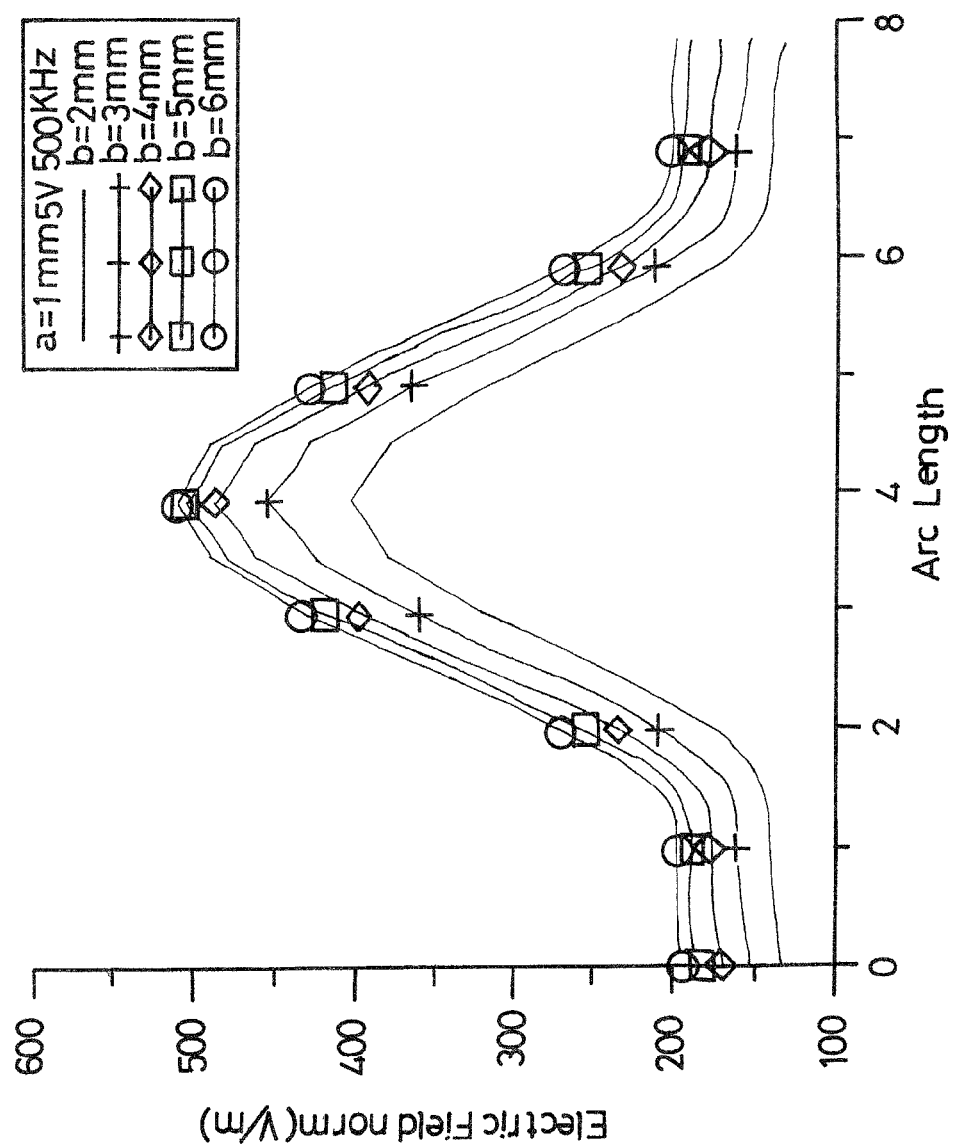
FIG. 5 is a graph showing the strength of the electromagnetic field produced by the electromagnetic stimulation device of FIG. 2 under various distances between the device's electrodes and the nerve to be stimulated.

Yet another embodiment of the present invention is described as follows. The preset voltage is set to 5V with frequency 500 KHz. The electrode width (a) of the positive and negative electrodes 12 and 13 is 1 mm, and the second distance (c) is 5 mm. Then, as shown in FIG. 5, where the electromagnetic field is measured when the first distance (b) between the positive and negative electrodes 12 and 13 is set to 2, 3, 4, 5, and 6 mm, respectively, it should be obvious that the electromagnetic field has a stronger strength when the first distance (b) is between 4 mm and 5 mm.

Figure 6:
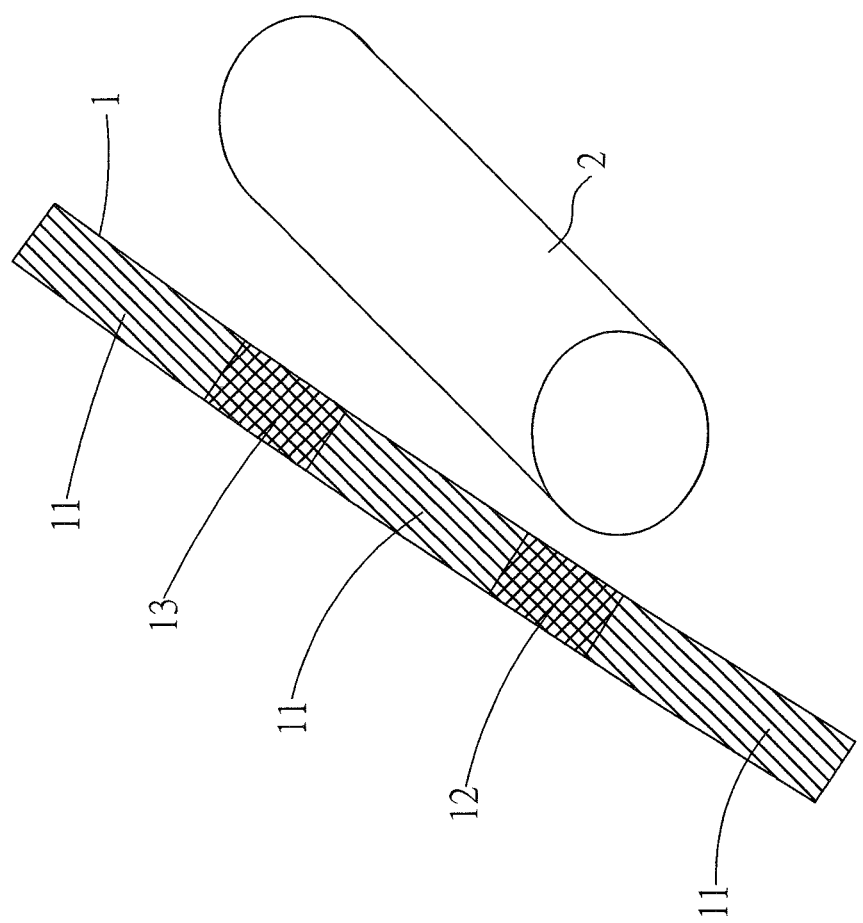
FIG. 6 is a schematic diagram showing a first embodiment of the electromagnetic stimulation device of FIG. 2.
Figure 7:
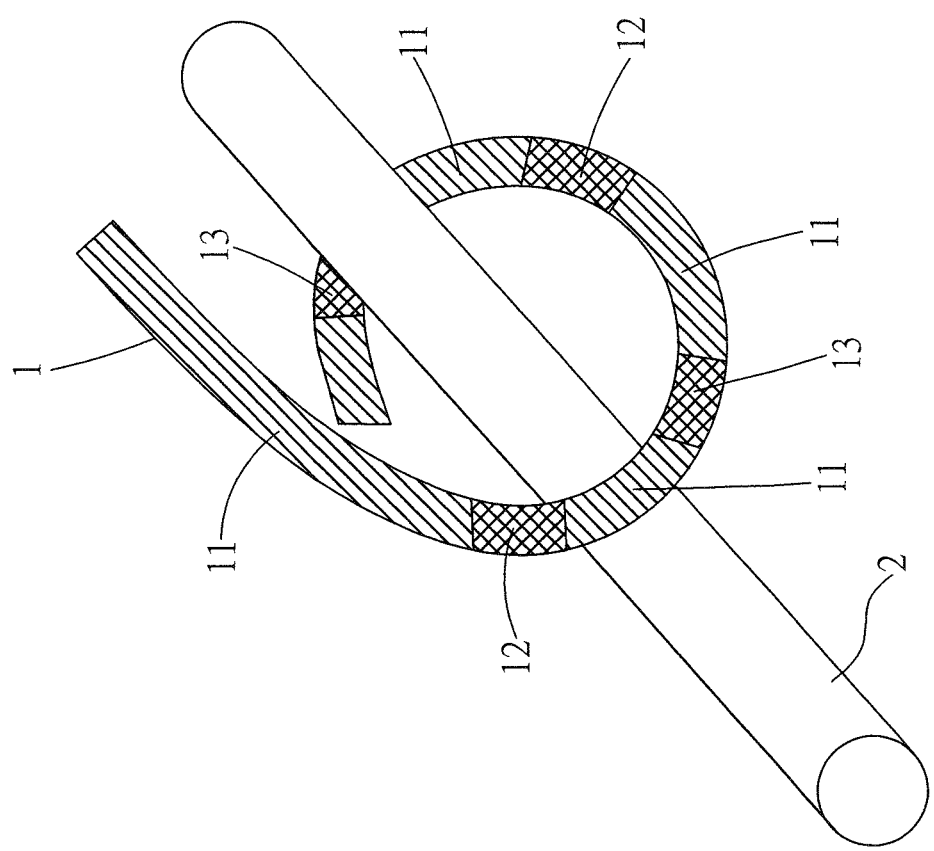
FIG. 7 is a schematic diagram showing a second embodiment of the electromagnetic stimulation device of FIG. 2.

As shown in FIGS. 2 and 6, the electromagnetic stimulation device 1 can have a linear shape. The electromagnetic stimulation device 1 contains at least one positive electrode 12 and at least one negative electrode 13. The positive and negative electrodes 12 and 13 are separated by the first distance (b). Then, the electromagnetic field produced by the positive and negative electrodes 12 and 13 are applied to the nerve 2 to conduct a low-power, low-temperature, high-frequency electromagnetic stimulation.

Figure 10:
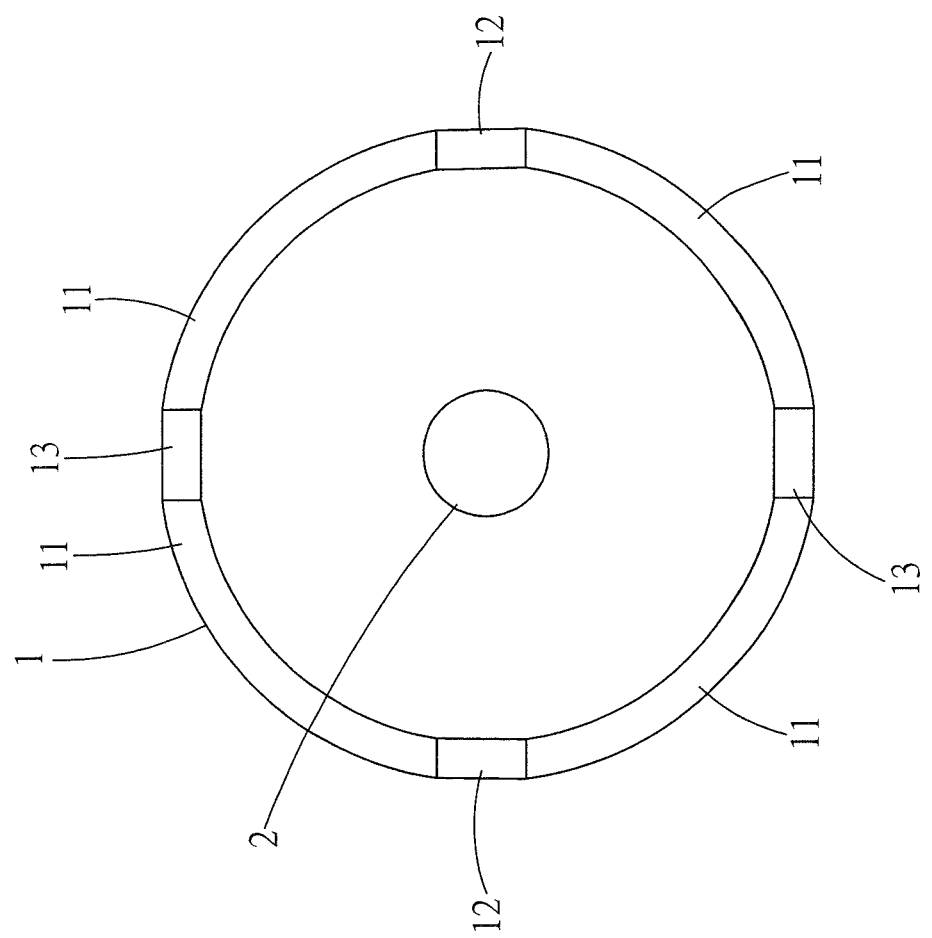
FIG. 10 is a schematic diagram showing an arrangement of the electrodes of the electromagnetic stimulation device of FIG. 7.
Figure 11:
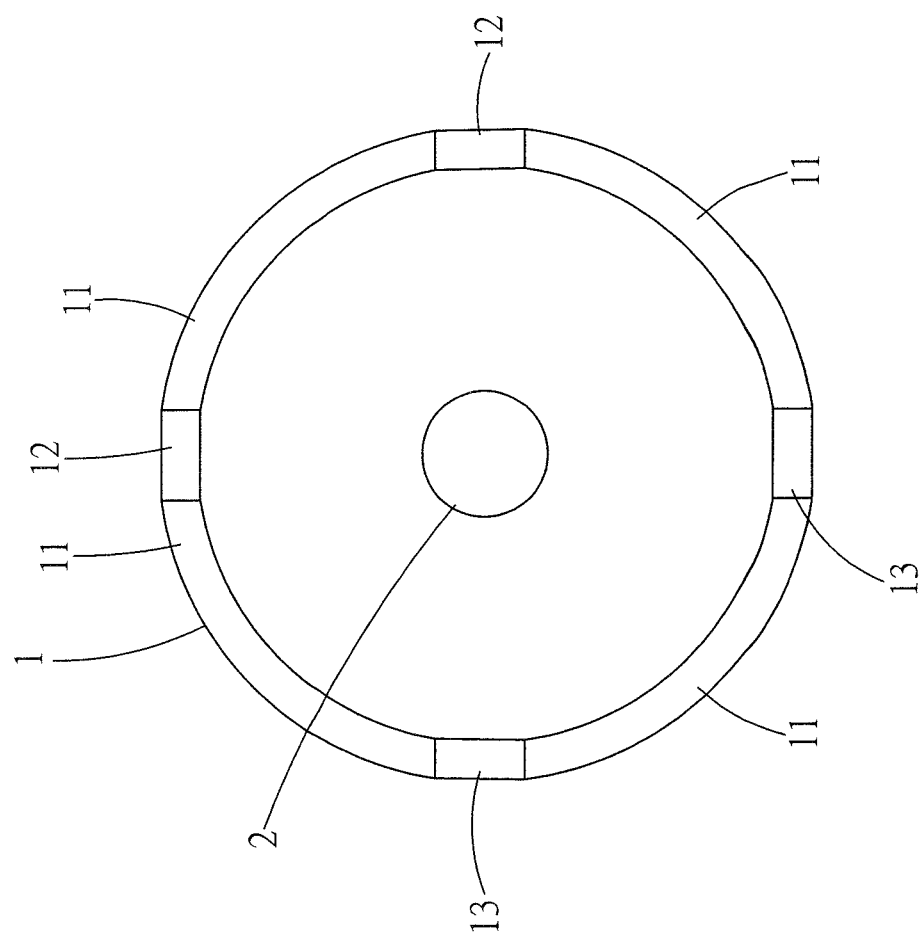
FIG. 11 is a schematic diagram showing another arrangement of the electrodes of the electromagnetic stimulation device of FIG. 7.
Figure 12:
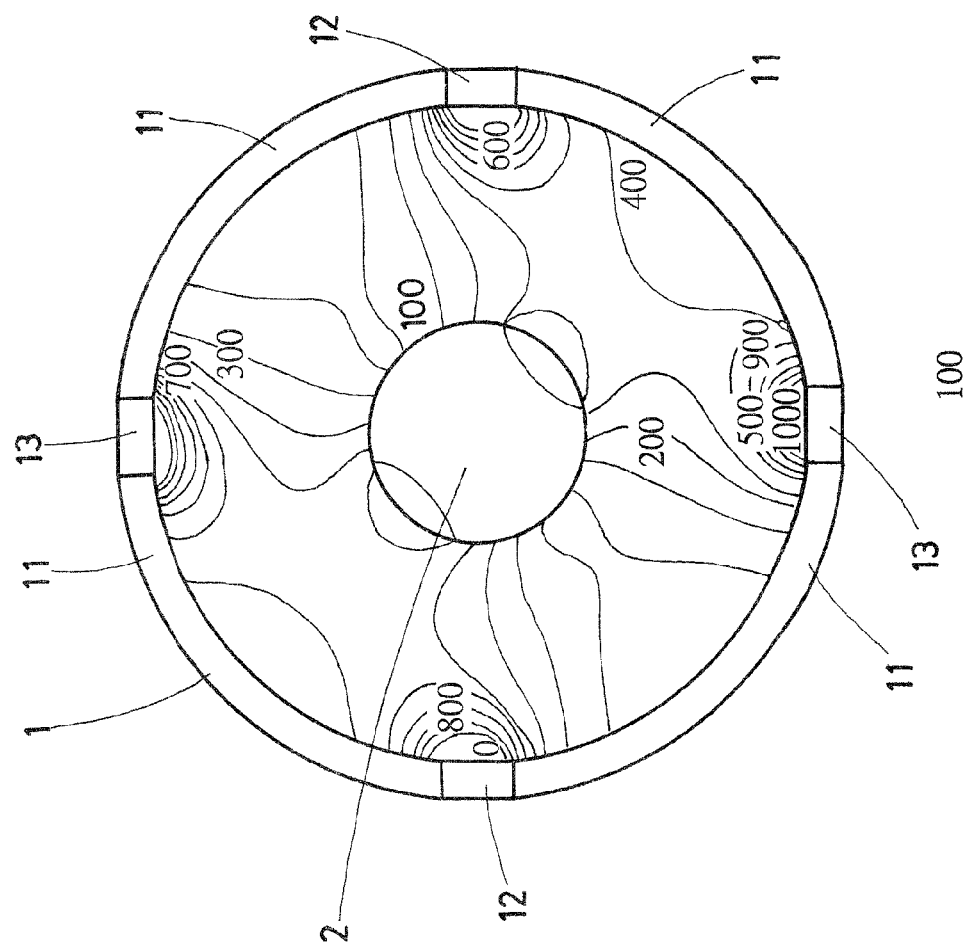
FIG. 12 is a graph showing the strength and pattern of the electromagnetic field produced by the electromagnetic stimulation device of FIG. 7.

As shown in FIGS. 7, 10, 11, and 12, the electromagnetic stimulation device 1 can have a ring shape. The electromagnetic stimulation device 1 contains at least two positive electrodes 12 and at least two negative electrodes 13, where the positive and negative electrodes 12 and 13 are arranged (e.g., as shown in FIG. 10) alternately around and at least at the second distance (c) from the nerve 2. Alternatively, the positive and negative electrodes 12 and 13 are arranged (e.g., as shown in FIG. 11) sequentially (not alternately) around and at least at the second distance (c) from the nerve 2. Then, as shown in FIG. 12, the electromagnetic field produced by the positive and negative electrodes 12 and 13 are applied to the nerve 2 to conduct a low-power, low-temperature, high-frequency electromagnetic stimulation. Again, the strength of the electromagnetic field is stronger as it is closer to the positive and negative electrodes 12 and 13.

Figure 8:
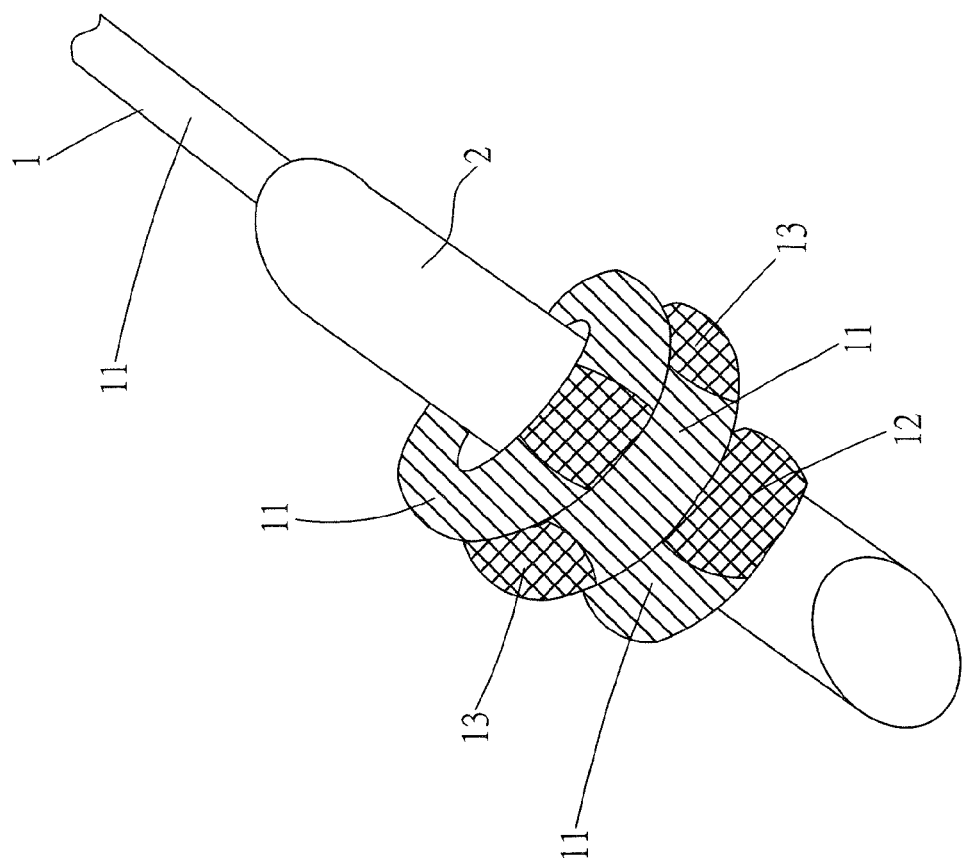
FIG. 8 is a schematic diagram showing a third embodiment of the electromagnetic stimulation device of FIG. 2.

As shown in FIG. 8, the electromagnetic stimulation device 1 can have a helix shape. The electromagnetic stimulation device 1 contains at least two positive electrodes 12 and at least two negative electrodes 13, where the positive and negative electrodes 12 and 13 can be arranged alternately or sequentially around and at least at the second distance (c) from the nerve 2. Then, the electromagnetic field produced by the positive and negative electrodes 12 and 13 are applied to the nerve 2 to conduct a low-power, low-temperature, high-frequency electromagnetic stimulation.

Figure 9:
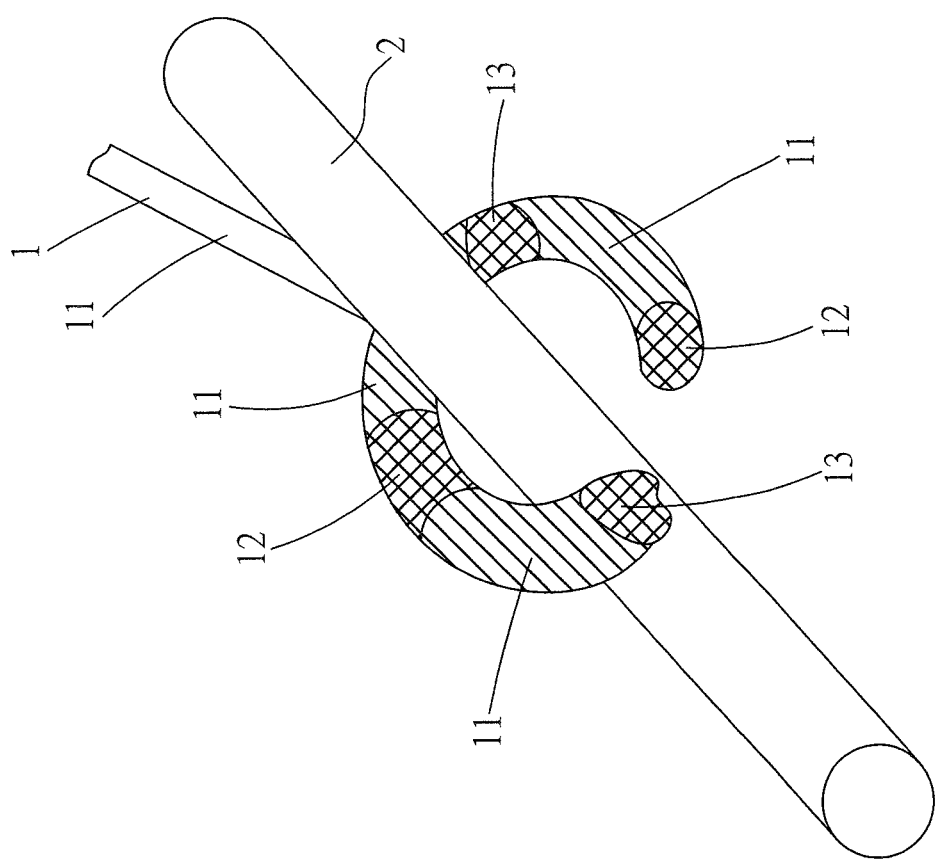
FIG. 9 is a schematic diagram showing a fourth embodiment of the electromagnetic stimulation device of FIG. 2.

As shown in FIG. 9, the electromagnetic stimulation device 1 can have a C-like shape. The electromagnetic stimulation device 1 contains at least two positive electrodes 12 and at least two negative electrodes 13, where the positive and negative electrodes 12 and 13 can be arranged alternately or sequentially around and at least at the second distance (c) from the nerve 2. Then, the electromagnetic field produced by the positive and negative electrodes 12 and 13 are applied to the nerve 2 to conduct a low-power, low-temperature, high-frequency electromagnetic stimulation.

Figure 13:
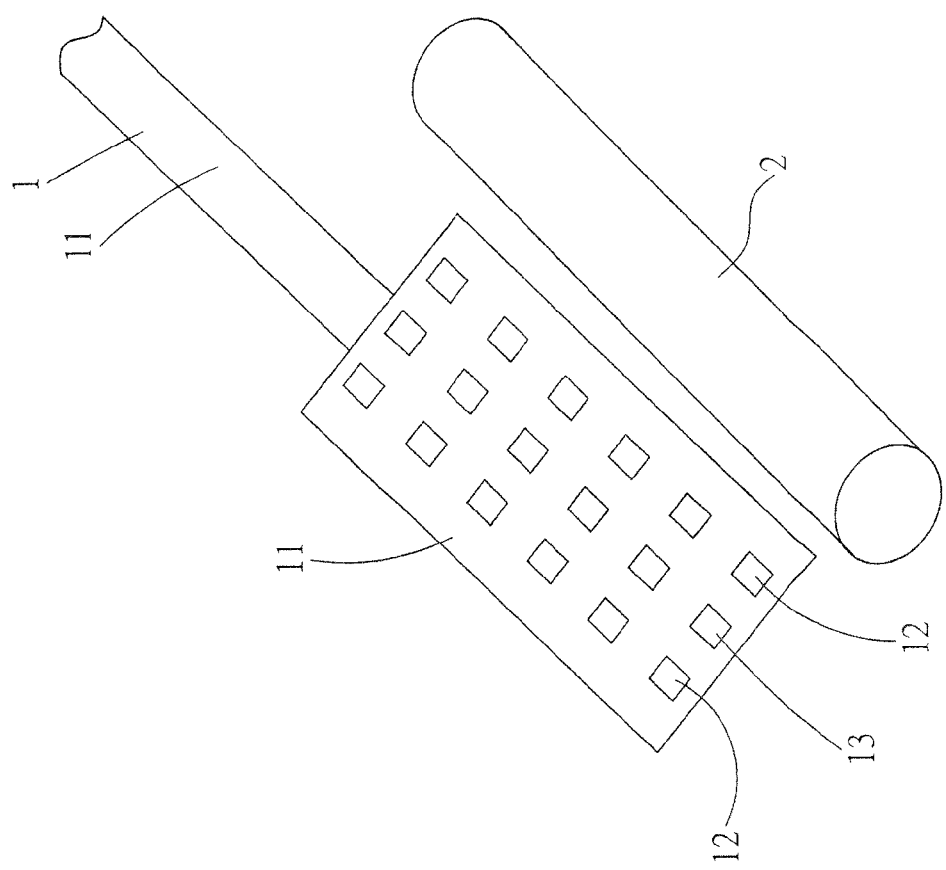
FIG. 13 is a schematic diagram showing a fifth embodiment of the electromagnetic stimulation device of FIG. 2.

As shown in FIG. 13, the electromagnetic stimulation device 1 can have a planar shape. The electromagnetic stimulation device 1 contains more than two positive electrodes 12 and more than two negative electrodes 13, where the positive and negative electrodes 12 and 13 can be arranged alternately or sequentially in an array at least at the second distance (c) from the nerve 2. Then, the electromagnetic field produced by the positive and negative electrodes 12 and 13 are applied to the nerve 2 to conduct a low-power, low-temperature, high-frequency electromagnetic stimulation.

Please note that electromagnetic stimulation device 1 can be embedded inside or installed outside human body. Either way the positive and negative electrodes 12 and 13 can be arranged alternately or sequentially at least at the second distance (c) from the nerve 2.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

We claim:

1. A pain management method of an electromagnetic stimulation device, wherein the electromagnetic stimulation device has at least a positive electrode and at least a negative electrode, and the positive and negative electrodes are separated by a first distance, the operation method comprising:
    positioning the electromagnetic stimulation device, which is at least at a second distance away from a nerve, wherein the second distance is a minimum linear distance between the electromagnetic stimulation device and the nerve, and the second distance is no more than 10 mm; and
    applying a preset voltage to the positive and negative electrodes so that an electromagnetic field covering and stimulating the nerve is produced between the positive and negative electrodes,
    wherein the preset voltage is no more than 10V and has a frequency between 200 KHz and 800 KHz.

2. The pain management method according to claim 1, wherein the preset voltage is between +3V and +10V, or between −3V and −10V, and the preset voltage has a frequency between 200 KHz and 800 KHz.

3. The pain management method according to claim 1, wherein each of the positive and negative electrodes has a width between 1 mm and 3 mm.

4. The pain management method according to claim 1, wherein the positive and negative electrodes are configured on an insulating member, and the first distance is between 3 mm and 7 mm.

5. The pain management method according to claim 1, wherein the electromagnetic stimulation device is configured to embed inside human body.

6. The pain management method according to claim 1, wherein the electromagnetic stimulation device is configured to install outside human body.

7. The pain management method according to claim 1, wherein the electromagnetic stimulation device is a linear shape, a ring shape, a C-like shape, a helix shape or a planar shape.

8. An implanted electromagnetic stimulation device for pain management, comprising at least a positive electrode and at least a negative electrode, wherein
    the positive and negative electrodes is separated by a first distance;
    the positive and negative electrodes are at least at a second distance away from a nerve to be stimulated, wherein the second distance is a minimum linear distance between the electromagnetic stimulation device and the nerve, and the second distance is no more than 10 mm;
    a preset voltage is applied to the positive and negative electrodes so that an electromagnetic field covering and stimulating the nerve is produced between the positive and negative electrodes; and
    the preset voltage is no more than 10V and has a frequency between 200 KHz and 800 KHz.

9. The implanted electromagnetic stimulation device according to claim 8, wherein the preset voltage is between +3V and +10V, or between −3V and −10V; and has a frequency between 200 KHz and 800 KHz.

10. The implanted electromagnetic stimulation device according to claim 8, wherein each of the positive and negative electrodes has a width between 1 mm and 3 mm.

11. The implanted electromagnetic stimulation device according to claim 8, wherein the electromagnetic stimulation device further comprises an insulating member; the positive and negative electrodes are configured on the insulating member; the first distance is between 3 mm and 7 mm.

12. The implanted electromagnetic stimulation device according to claim 8, wherein the electromagnetic stimulation device has a linear shape.

13. The implanted electromagnetic stimulation device according to claim 8, wherein the electromagnetic stimulation device has a ring shape, and comprises at least two positive electrodes and at least two negative electrodes arranged around and at least at the second distance from the nerve.

14. The implanted electromagnetic stimulation device according to claim 8, wherein the electromagnetic stimulation device has a C-like shape, and comprises at least two positive electrodes and at least two negative electrodes arranged around and at least at the second distance from the nerve.

15. The implanted electromagnetic stimulation device according to claim 8, wherein the electromagnetic stimulation device has a helix shape, and comprises at least two positive electrodes and at least two negative electrodes arranged around and at least at the second distance from the nerve.

16. The implanted electromagnetic stimulation device according to claim 8, wherein the electromagnetic stimulation device has a planar shape, and comprises more than two positive electrodes and more than two negative electrodes arranged in an array and at least at the second distance from the nerve.

* * * * *